United States Patent [19]

Cheney et al.

[11] Patent Number: 4,939,179

[45] Date of Patent: Jul. 3, 1990

[54] COSMETIC EMULSIONS WITH HYDROCARBON THICKENING AGENTS

[75] Inventors: Michael C. Cheney, Fairfield; Dipak K. Ghosh, Monroe; Lorraine Williams, Stamford; Philip D. Ziegler, Oxford, all of Conn.

[73] Assignee: Chesebrough-Pond's Inc., Greenwich, Conn.

[21] Appl. No.: 369,781

[22] Filed: Jun. 22, 1989

[51] Int. Cl.$^5$ .............................................. A61K 47/00
[52] U.S. Cl. .................... 514/789; 514/772; 514/844
[58] Field of Search ................. 514/789, 76, 772, 844

[56] References Cited

U.S. PATENT DOCUMENTS

| | | | |
|---|---|---|---|
| 3,634,265 | 1/1972 | Merritt | 252/107 |
| 3,818,105 | 6/1974 | Coopersmith et al. | 514/789 |
| 4,481,186 | 11/1984 | Deckner | 514/847 |

Primary Examiner—Douglas W. Robinson
Assistant Examiner—Zohreh A. Fay
Attorney, Agent, or Firm—Milton L. Honig

[57] ABSTRACT

An aqueous cosmetic emulsion is provided that includes an isoparaffin and an alkyl phosphate salt wherein the relative ratio of isoparaffin to alkyl phosphate sale ranges from about 40:1 to 1:1. The combination of isoparaffin with alkyl phosphate salt provides an unexpected thickening effect and results in a non-greasy product relative to a mineral oil bearing formula.

9 Claims, No Drawings

COSMETIC EMULSIONS WITH HYDROCARBON THICKENING AGENTS

BACKGROUND OF THE INVENTION

1. Field of the Invention

The invention relates to a cosmetic emulsion with a special thickening agent that provides a product having improved aesthetics and skin feel.

2. The Related Art

Various emollient creams and lotions have been used to alleviate the signs and symptoms of dry skin. The application of these products help return skin to a normal, moisturized condition by the process of occlusion and humectancy. Historically, a performance dichotomy has always existed, wherein, those ingredients such as glycerin and petroleum jelly found to be effective in the treatment of dry skin, have been cosmetically unacceptable due to their heaviness. This is especially true as you increase the concentration of these materials in a finished emulson product. Therefore, ingredients such as mineral and silicone oils are used by formulators to increase lubricity of a formulation, thereby, decreasing the perception of heaviness related to the materials such as glycerin and petroleum jelly.

U.S. Pat. No. 3,818,105 (Coopersmith et al.) teaches the usefulness of $C_{12}$-$C_{14}$ isoparaffinic hydrocarbons as effective skin lubricants in cosmetic preparations. These hydrocarbons were disclosed as being typically admixed with water, monoalkanols, organic esters, polyhydroxy compounds, lanolin, minerals, colorants, surfactants, waxes and perfumes. Example 5 reports a hand cleaner composition whose major ingredients are isoparaffin, oleic acid and nonylphenol (10) ethoxylate, the latter a nonionic surfactant.

U.S. Pat. No. 3,634,265 (Merritt) reports use of a liquid isoparaffinic hydrocarbon as a solvent for skin contaminents in a skin cleaner emulsion. Among the further components listed are a light mineral oil, a long-chain alkanoic acid neutralized with an alkanolamine, an anionic surfactant, a protective colloid and deionized water.

While the aforementioned art has recognized the usefulness of isoparaffinic hydrocarbons, as lubricants or solvents, there has been no mention as to how these materials effect product viscosities. Often one of the more difficult problems in formulating high water system is the search for thickening agents which provide the correct viscosity but do not detract from skin performance properties. Some thickeners provide sufficient body but impart unacceptable greasiness. Moreover, one ingredient frequently renders another physically incompatible resulting in phase separation of the composition. Examples of the aforementioned patents suggest use of rather high levels (greater than 10%) of isoparaffin and no higher than 60% water. There has been no indication as to the affect, if any, of relatively low isoparaffin levels in the presence of a relatively high water concentration. Furthermore, the role of surfactant has not been fully defined in this art.

Consequently it is an object of the present invention to provide a cosmetic emulsion which when applied to the skin will have sufficient viscosity to render it aesthetically pleasing while at the same time avoid a greasy feeling that some thickeners would normally impart.

A further object of the present invention is to provide a hand and body lotion of proper pH and good phase stability.

These and other objects of the invention will more fully be appreciated through the detailed description that follows.

SUMMARY OF THE INVENTION

An aqueous cosmetic emulsion is provided comprising the following components:
i) an isoparaffin; and
ii) an alkyl phosphate salt;
wherein the isoparaffin and alkyl phosphate salt are present in a respective weight ration of from about 40:1 to about 1:1.

DETAILED DESCRIPTION OF THE INVENTION

The present invention describes an aqueous cosmetic emulsion having a consumer pleasing viscosity while at the same time being non-greasy to the skin. Isoparaffins have been discovered to have exceptional thickening properties even though present at relatively low concentration in the aqueous system. Furthermore it has been discovered that certain types of surfactants interact with isoparaffins to improve the thickening effect of the latter. Also noted has been the critical nature of the relative ratios of the oil to the surfactant. A still further discovery has been the reduction in greasiness through use of isoparaffins as replacement for straight-chain hydrocarbon oil.

Isoparaffins of the present invention are largely saturated aliphatic hydrocarbon with highly branched structures having from 11 to 13 carbons atoms per molecule. Preferably the isoparaffins are selected from one or a mixture of isomeric species including:

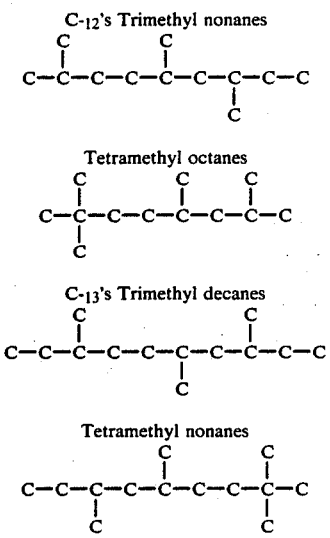

A particularly preferred type of isoparaffin is a material known as Isopar L, sold by the Exxon Company, Houston, Tex. The material is a clear, odorless and colorless thin liquid with a flash point of 142° F. Isopar L has an average molecular weight of 171 and a viscosity of 2.6 centistokes at 15.5° C.

Isoparaffin normally will be incorporated into the compositions of this invention in an amount from about 0.5 to about 5% by weight of the total. Preferably this material will be present in an amount from about 1% to about 3%, optimally between about 1 and about 2% by weight of the total formulation.

As mentioned earlier, a second critical component of the composition is the presence of a selected surfactant, namely an alkyl phosphate salt. More particularly, the surfactant should be a salt of a $C_8$-$C_{22}$ alkyl phosphate. Illustrative surfactants include salts of cetyl phosphate, myristyl phosphate, lauryl phosphate and stearyl phosphate. Salt counterions may be selected from alkali-metal, ammonium, trialkylammonium and di- or tri-alkanolammonium cations. Particularly preferred is diethanolammonium cetyl phosphate, commercially available under the trademark Amphisol from the Givaudan Corporation. The amount of alkyl phosphate salt will range from about 0.1% to about 3% by weight of the total formulation. Particularly preferred is a concentration from about 0.25% to about 1%, optimally between about 0.25% and 0.5%. According to the present invention it is important to incorporate isoparaffin and alkyl phosphate salt in a relative weight ratio which falls within the range from about 40:1 to about 1:1, preferably from about 20:1 to about 4:1, optimally between about 10:1 and about 6:1.

By selection of isoparaffin and alkyl phosphate salt as well as careful control of the relative ratios, it has become possible to thicken an aqueous system with a minimum amount of oily material. Consumer acceptable viscosities are herewith achieved which may range from 35 to about 90, preferably from about 50 to about 70 units as measured with a Brookfield Viscometer LVT Model using #4 spindle at 60 rmp at 25° C. @15 revolutions.

Water is of course a major component of the compositions described by this invention. The amount of water will range in amount anywhere from about 50% up to about 95% by weight of the total formulation. Preferably the amount of water will be present in amount from about 80% to about 92%, optimally between about 87 and 90% by weight.

Beyond the aforementioned essential components, the cosmetic compositions of the present invention may also contain other ingredients typically found in such formulations. Besides isoparaffin there may also be included from 0.1 to 2% of mineral oil comprising liquid hydrocarbons that are substantially non-isoparaffinic. For emulsification and emollient purposes there may be incorporated from 0.1% to 20% of a wax (e.g carnauba or microcrystalline polyethylene wax), a lanolin derived material (e.g. Acetulan which is a 9:1 mixture of cetyl acetate and acetyl lanolin alcohol available from Amerchol), stearols (e.g. glycerol monostearate and stearamide AMP and mixtures thereof sold by the Van Dyke Co. under the mark Cerasynt IP), fatty alcohols (e.g. stearic acid available under the trademark Neofat) and mixtures of these ingredients. There may also be present from about 0.01 to 2% of adjunct water-phase thickening agents such as Veegum, a magnesium aluminum silicate sold by the Vanderbilt Chemical Co., and Carbopol 934, a cross-linked polyacrylate polymer available from the B.F. Goodrich Co. Proteins as well as silicone oils may be included to improve skin feel. Other minor but important functional ingredients such as colorant, fragrance and preservative are normally also included, each present in an effective amount to accomplish its function. Suitable preservatives include the methyl and propyl parabens and sodium ethylenediaminetetraacetates. All the foregoing materials are more fully illustrated in *Cosmetics, Science & Technology*, 2 ed., Ed. Board -M.S. Balsom et al. and *Cosmetic and Toileting Formulations*, E. W. Flick, Noyes Publications, 1984, the disclosures of which are incorporated herein by reference.

Compositions of the present invention generally have a cream or lotion consistency and may be in the form of either an oil-in-water or water-in-oil emulsion. The former type emulsion having a continuous water phase is the preferred embodiment since it has more pleasing cosmetic properties. These compositions are useful in the treatment of dry skin. They can be applied to the skin in an amount sufficient to meet an individual users needs and desires.

The following examples will more fully illustrate the embodiments of the invention. All parts, percentages and proportions referred to herein and in the appended claims are by weight unless otherwise indicated.

EXAMPLE 1

A variety of viscosity and skin feel tests were conducted with the following base formula:

| BASE FORMULA | |
|---|---|
| Ingredients | Weight % |
| Deionized Water | Q.S. |
| Glycerin | 5.0 |
| Glycerol Monostearate | 2.0 |
| Cetyl Alcohol | 0.1 |
| Veegum | 0.05 |
| Triethanolamine | 0.72 |
| Stearic Acid | 2.0 |
| Amphisol | Varies |
| Mineral Oil (or) Isopar L | Varies |

EXAMPLE 2

A series of skin feel tests were conducted employing the base formula of Example 1. Results of these tests are reported in Tables I through V.

TABLE I

10% MINERAL OIL -vs- 10% ISOPAR L
BOTH CONTAINING 0.25% AMPHISOL (40:1 Ratio)

| SUBJECT # | 10% MINERAL OIL 0.25% AMPHISOL | 10% ISOPAR L 0.25% AMPHISOL | RATING DIFFERENCE |
|---|---|---|---|
| 1 | 7 | 9 | −2 |
| 2 | 10 | 10 | 0 |
| 3 | 8 | 6 | +2 |
| 4 | 9 | 2 | +7 |
| 5 | 8 | 5 | +3 |
| 6 | 9 | 7 | +2 |
| 7 | 6 | 3 | +3 |
| 8 | 7 | 4 | +3 |
| 9 | 8 | 6 | +2 |
| 10 | 10 | 9 | +1 |
| 11 | 3 | 1 | +2 |
| X ± S.D. = | 7.73 ± 2.00 | 5.64 ± 2.9 | 2.1 ± 2.2 |

I. Hand and Body Lotions ratings on scale 1-10
(1) non-greasy
(10) very greasy
II. Subjects were asked which product was the least greasy: 10% Mineral Oil/0.25% Amphisol (or) 10% Isopar L/0.25% Amphisol. Nine out of eleven chose the Isopar L formula as being less greasy.

TABLE II

5% MINERAL OIL -vs- 5% ISOPAR L
BOTH CONTAINING 0.5% AMPHISOL (10:1 Ratio)

| SUBJECT # | 5% MINERAL OIL 0.5% AMPHISOL | 5% ISOPAR L 0.5% AMPHISOL | RATING DIFFERENCE |
|---|---|---|---|
| 1 | 2 | 10 | −8 |
| 2 | 5 | 9 | −4 |
| 3 | 3 | 4 | −1 |
| 4 | 8 | 4 | +4 |
| 5 | 4 | 2 | +2 |
| 6 | 3 | 1 | +2 |
| 7 | 6 | 4 | +2 |
| 8 | 6 | 5 | +1 |
| 9 | 7 | 3 | +4 |
| 10 | 8 | 3 | +5 |
| 11 | 9 | 6 | +3 |
| X ± S.D. = | 5.55 ± 2.3 | 4.64 ± 2.8 | 0.91 ± 3.9 |

I. Hand and Body Lotion ratings on scale of 1-10
(1) non-greasy
(10) very greasy
II. Subjects were asked which product was the least greasy: 5% Mineral Oil/0.5% Amphisol (or) 5% Isopar L/0.5% Amphisol. Eight out of Eleven chose the Isopar L formula as being less greasy.

TABLE III

2.5% MINERAL OIL vs. 2.5% ISOPAR
BOTH CONTAINING 0.25% AMPHISOL (10:1 RATIO)

| SUBJECT # | 2.5% MINERAL OIL 0.25% AMPHISOL | 2.5% ISOPAR L 0.25% AMPHISOL | RATINGS DIFFERENCE |
|---|---|---|---|
| 1 | 3 | 2 | +1 |
| 2 | 4 | 3 | +1 |
| 3 | 3 | 1 | +2 |
| 4 | 2 | 5 | −3 |
| 5 | 5 | 7 | −2 |
| 6 | 5 | 8 | −3 |
| 7 | 5 | 2 | +3 |
| 8 | 8 | 2 | +6 |
| 9 | 2 | 2 | 0 |
| 10 | 6 | 2 | +4 |
| 11 | 9 | 5 | +4 |
| 12 | 7 | 3 | +4 |
| X ± S.D. | 4.92 ± 2.18 | 3.5 ± 2.14 | 1.42 ± 2.84 |

I. Hand and Body Lotion ratings on scale of 1-10
(1) non-greasy
(10) very greasy
II. Subjects were asked which product was the least greasy 2.5% Mineral Oil 0.25% Amphisol (or) 2.5% Isopar L/0.25% Amphisol. Eight out of eleven chose the Isopar L formula as being less greasy.

TABLE IV

1% MINERAL OIL -vs- 1% ISOPAR L
BOTH CONTAINING 0.25% AMPHISOL (4:1 RATIO)

| SUBJECT # | 1% MINERAL OIL 0.25% AMPHISOL | 1% ISOPAR L 0.25% AMPHISOL | RATING DIFFERENCE |
|---|---|---|---|
| 1 | 6 | 4 | +2 |
| 2 | 6 | 3 | +3 |
| 3 | 7 | 5 | +2 |
| 4 | 7 | 3 | +4 |
| 5 | 9 | 4 | +5 |
| 6 | 6 | 2 | +4 |
| 7 | 7 | 5 | +2 |
| 8 | 1 | 1 | 0 |
| 9 | 5 | 7 | −2 |
| 10 | 3 | 3 | 0 |
| X ± S.D. | 5.7 ± 2.18 | 3.7 ± 1.62 | 2 ± 2.05 |

I. Hand and Body Lotion ratings on a scale of 1-10
(1) non-greasy-(10) very greasy
II. Subjects were asked which product was the least greasy: 1% Mineral Oil/0.25% Amphisol (or) 1% Isopar L/0.25% Amphisol. Six out of ten chose the Isopar L formula as being less greasy.

TABLE V

0.25% MINERAL OIL -vs- 0.25% ISOPAR L
BOTH CONTAINING 0.25% AMPHISOL

| SUBJECT # | 0.25% MINERAL OIL 0.25% AMPHISOL | 0.25% ISOPAR L 0.25% AMPHISOL | RATING DIFFERENCE |
|---|---|---|---|
| 1 | 10 | 9 | +1 |
| 2 | 9 | 1 | +8 |
| 3 | 9 | 3 | +6 |
| 4 | 9 | 2 | +7 |
| 5 | 9 | 4 | +5 |
| 6 | 8 | 3 | +5 |
| 7 | 10 | 2 | +8 |
| 8 | 9 | 8 | +1 |
| 9 | 8 | 9 | −1 |
| 10 | 2 | 10 | −8 |
| 11 | 1 | 2 | −1 |
| 12 | 6 | 7 | −1 |
| X ± S.D. = | 7.5 ± 2.87 | 5 ± 3.19 | 2.5 ± 4.63 |

I. Hand and Body Lotion ratings on a scale of 1-10
(1) non-greasy
(10) very greasy
II. Subjects were asked which product was the least greasy 0.25% Mineral Oil/0.25% Amphisol (or) 0.25% Isopar L/0.25% Amphisol. Six out of eleven chose the Isopar L formula as being less greasy.

From the foregoing results it is evident that at ratios of hydrocarbon to surfactant of 40:1 to 1:1 isoparaffin-type hydrocarbon is much preferred over mineral oil.

EXAMPLE 3

Viscosity effects from the interaction of Amphisol with mineral oil versus that of isoparaffin are herein reported. The base formula of Example 1 was employed for these tests.

TABLE VI

VISCOSITY OF VARIOUS LEVELS OF AMPHISOL WITH 1% MINERAL OIL (or) 1% ISOPAR L

| | VISCOSITY (BROOKFIELD UNITS) | |
|---|---|---|
| % AMPHISOL | 1% MINERAL OIL | 1% ISOPAR L |
| 0.10 | 28.5 | 48.5 |
| 0.25 | 33.0 | 84.0 |
| 0.40 | 43.5 | 57.5 |
| 0.50 | 40.5 | 61.0 |
| 1.00 | 56.0 | 76.0 |
| 2.00 | 10.0 | 18.0 |

TABLE VII

VISCOSITY OF VARIOUS LEVELS OF MINERAL OIL (OR) ISOPAR L WITH 0.5% AMPHISOL

| | VISCOSITY (BROOKFIELD UNITS) | |
|---|---|---|
| WEIGHT % | MINERAL OIL | ISOPAR L |
| 1.0 | 40.5 | 61.0 |
| 2.0 | 39.5 | 55.0 |
| 3.0 | 44.0 | 45.0 |
| 4.0 | 23.0 | 45.5 |
| 5.0 | 30.0 | 40.5 |

TABLE VIII

VISCOSITIES USING TWO LEVELS OF MINERAL OIL (OR) ISOPAR L WITHOUT AMPHISOL

| | VISCOSITY (BROOKFIELD UNITS) | |
|---|---|---|
| WEIGHT % | MINERAL OIL | ISOPAR L |
| 1.0 | 15.0 | 27.0 |
| 5.0 | 19.5 | 32.0 |

TABLE IX

VISCOSITIES USING TWO LEVELS OF
MINERAL OIL (OR) ISOPAR L WITH 0.25% AMPHISOL

| WEIGHT % | VISCOSITY (BROOKFIELD UNITS) | |
|---|---|---|
| | MINERAL OIL | ISOPAR L |
| 5.0 | 27.0 | 32.0 |
| 10.0 | 31.5 | 41.0 |

As can be seen in Tables VI through IX, the combination of Amphisol with Isopar L is much more effective as a thickening agent than the Amphisol combination with mineral oil. This thickening effect was unexpected because straight mineral oil has a viscosity of 19.0 Brookfield units as compared with the much lighter Isopar L having 2.8 Brookfield unit viscosity.

| RAW MATERIAL VISCOSITY READINGS | | | |
|---|---|---|---|
| | BROOKFIELD UNITS | | CPS |
| DEIONIZED WATER | 02.3 | (#1 60 RPM 60 SEC.) | 2.3 |
| GLYCERIN | 45.8 | (#3 60 RPM 60 SEC.) | 916.0 |
| TRIETHANOLAMINE | 30.8 | (#3 60 RPM 60 SEC.) | 616.0 |
| MINERAL OIL | 19.0 | (#1 60 RPM 60 SEC.) | 19.0 |
| $C_{11}$-$C_{13}$ ISOPAR L | 02.8 | (#1 60 RPM 60 SEC.) | 2.8 |
| SODIUM LAURYL ETHER SULFATE | 53.8 | (#4 60 RPM 60 SEC.) | 5380.0 |
| GLYCERYL STEARATE | SOLID | | |
| CETYL ALCOHOL | SOLID | | |
| MAGNESIUM ALUMINUM SILICATE (VEEGUM) | SOLID | | |
| STEARIC ACID (NEOFAT) | SOLID | | |
| DEA CETYL PHOSPHATE (AMPHISOL) | SOLID | | |
| 100% SODIUM LAURYL SULFATE | SOLID | | |
| QUATERNARY AMMONIUM COMPOUNDS | SOLID | | |
| ETHOXYLATED FATTY ALCOHOLS | SOLID | | |

EXAMPLE 4

Illustrated here is the effect of surfactants other than Amphisol in the base formula of Example 1. Table X demonstrates that the cationic surfactant Arosurf and nonionic surfactant Brij 35 do not interact with Isopar L to thicken the base formula relative to that of mineral oil. The mineral oil formula has higher viscosity in both instances. Only anionic surfactants such as lauryl ether sulfate, lauryl sulfate and DEA cetyl phosphate appear to interact with Isopar L to thicken the base formula. However, it is only with the DEA cetyl phosphate, i.e. Amphisol, that there is achieved a viscosity hgiher than 35 Brookfield Units. Viscosities lower than 35 Brookfield Units are undesirably watery in hand or body cosmetic lotions.

TABLE X

VISCOSITIES OF BASE FORMULA INCORPORATING
VARIOUS SURFACTANTS AT 0.5% WITH 1% MINERAL OIL OR ISOPAR L

| SURFACTANTS | VISCOSITY (BROOKFIELD UNITS) | |
|---|---|---|
| | 1% MINERAL OIL | 1% ISOPAR L |
| SODIUM LAURYL ETHER SULFATE | 16.5 | 23.0 |
| 100% SODIUM LAURYL SULFATE | 1.5 | 6.5 |
| DISTEARYLDIMONIUM CHLORIDE (AROSURF) | 49.0 | 34.5 |
| LAURETH-23 (BRIJ 35) | 3.0 | 2.5 |
| DEA CETYL PHOSPHATE (AMPHISOL) | 40.5 | 61.0 |

The foregoing description and examples illustrate select embodiments of the present invention. In light thereof, various modifications will be suggested to one skilled in the art, all of which are within the purview of this invention.

What is claimed is:

1. An aqueous cosmetic emulsion comprising:
   i) an isoparaffin;
   ii) a $C_8$-$C_{22}$ alkyl phosphate salt;
   wherein the isoparaffin and alkyl phosphate salt are present in a respective weight ratio of from about 40:1 to about 1:1, and said emulsion having a viscosity ranging from 35 to about 90 Brookfield units as measured with a Brookfield Viscometer Model LVT using a #4 spindle rotating at 60 rpm at 25° C.

2. Ann aqueous cosmetic emulsion according to claim 1 wherein said ratio ranges from about 10:1 to about 4:1.

3. An aqueous cosmetic emulsion according to claim 1 wherein said viscosity ranges from about 50 to about 70 Brookfield Units.

4. An aqueous cosmetic emulsion according to claim 1, wherein the salt is a cetyl phosphate salt.

5. An aqueous cosmetic emulsion according to claim 4 wherein said salt is diethanolamine cetyl phosphate.

6. An aqueous cosmetic emulsion according to claim 1 wherein the isoparaffin is present in an amount from about 0.5 to about 5% by weight.

7. An aqueous cosmetic emulsion according to claim 1 wherein isoparaffin is present in an amount from about 1% to 2% by weight.

8. An aqueous cosmetic emulsion according to claim 1 wherein water is present from about 80% to about 92% by weight.

9. An aqueous cosmetic emulsion according to claim 1 wherein the isoparaffin is selected from a $C_{11}$ to a $C_{13}$ material and mixtures thereof.

* * * * *